(12) United States Patent
Alraddadi et al.

(10) Patent No.: US 12,153,115 B2
(45) Date of Patent: Nov. 26, 2024

(54) REMOTE DIAGNOSTIC DEVICE FOR MRI COIL TESTING AND METHOD OF USE

(71) Applicants: Fahad Alraddadi, Pittsburgh, PA (US); William Monski, Sewickley, PA (US); Tobias Sun, Wexford, PA (US)

(72) Inventors: Fahad Alraddadi, Pittsburgh, PA (US); William Monski, Sewickley, PA (US); Tobias Sun, Wexford, PA (US)

( * ) Notice: Subject to any disclaimer, the term of this patent is extended or adjusted under 35 U.S.C. 154(b) by 0 days.

(21) Appl. No.: 17/673,522

(22) Filed: Feb. 16, 2022

(65) Prior Publication Data
US 2024/0310467 A1     Sep. 19, 2024

Related U.S. Application Data (60) Provisional application No. 63/192,799, filed on May 25, 2021, provisional application No. 63/192,772, filed on May 25, 2021, provisional application No. 63/149,896, filed on Feb. 16, 2021.

(51) Int. Cl.
    *G01V 3/00*     (2006.01)
    *A61B 5/055*     (2006.01)
    *G01R 33/58*     (2006.01)

(52) U.S. Cl.
    CPC ............ *G01R 33/583* (2013.01); *A61B 5/055* (2013.01)

(58) Field of Classification Search
    CPC ........ G01R 33/34007; G01R 33/34046; G01R 33/481; G06T 11/005; G06T 2110/41
    USPC .......................................................... 324/322
    See application file for complete search history.

(56) References Cited

U.S. PATENT DOCUMENTS

2018/0172786 A1* 6/2018 Patulea .............. G01R 33/3621

FOREIGN PATENT DOCUMENTS

CN     107847181 A * 3/2018 ............. A61B 5/055

* cited by examiner

*Primary Examiner* — Walter L Lindsay, Jr.
*Assistant Examiner* — Frederick Wenderoth
(74) *Attorney, Agent, or Firm* — Gary P. Topocosky (57) ABSTRACT

A device for remotely diagnosing an MRI coil comprises: a Diagnostic Interface Device (or DID); means for plugging the MRI coil into the DID when the MRI coil is not in use, said device adapted for: (a) measuring the status of certain key electrical conditions for the coil; (b) receiving a response back from the signals initially aimed at the coil in question; (c) processing those responses received; and (d) transferring the measured electronic status (using a specific code number for the coil) to a remote storage area on the internet. A method of use is also disclosed.

20 Claims, 6 Drawing Sheets

REMOTE DIAGNOSTIC DEVICE FOR MRI COIL TESTING AND METHOD OF USE

REFERENCE TO RELATED APPLICATIONS

This application is a perfection of Provisional Application Ser. No. 63/149,896, filed on Feb. 16, 2021, Application Ser. No. 63/192,772, filed on May 25, 2021 and Application Ser. No. 63/192,799, also filed on May 25, 2021, all three disclosures of which are fully incorporated by reference herein.

STATEMENT OF GOVERNMENT INTEREST

Not Applicable

STATEMENT AS TO RIGHTS TO INVENTIONS MADE UNDER FEDERALLY SPONSORED RESEARCH OR DEVELOPMENT

Not Applicable.

NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

(1) Field of the Invention

The present invention relates to a coil monitoring device or system, as well as a method for using the same to predict a failure (soft or hard) of one or more coils for a magnetic resonance imaging (MRI) apparatus. Alternate embodiments of this invention may be embedded into new or existing MRI machines. A handheld variation is also envisioned. The dashboard display for use with the foregoing versions includes proprietary elements. The various inventions may be marketed tinder the "Echo" brand name.

A magnetic resonance inaging (MRI) apparatus that performs magnetic image processing of a patient, the body part of a patient, or possibly an inanimate object. Such apparatus include a magnet system with a plurality (i.e., one or more) magnetic coils that form a gradient magnetic field and a static magnetic field. The typical MRI apparatus includes both an RF coil element and a DC element.

For a magnetic resonance inaging apparatus that uses a superconducting magnet, once a coil failure occurs, the operating state of the apparatus/system is compromised. Either a fuzzy, unusable image results (a soft fail) or the machine produces no image whatsoever (a hard fail).

The Internet of Things (IoT) is used in a variety of applications. This invention will be useful to owners and operators of MRI apparatus. This invention will save time and money but most importantly, it will improve patient care by identifying MRI coil failures before they occur.

This invention will monitor important characteristics of an MRI coil when the MRI apparatus/machine is not in use. The device hereinbelow will transmit resulting monitored data to applicable MRI service organizations and end users. When used, this invention will help detect a soft or a hard failure of one or more of the MRI coils in an apparatus.

MRI machines are an important diagnostic tool used in modern medicine every day. MRI coils are essential components of those machines. These coils are necessary for acquiring the MR images generated by such MRI equipment. Currently, there is no way to know when an MRI coil is going to fail until it is being utilized during an MRI exam. When an MRI coil fails, the MRI procedure must be stopped, and the MRI exam rescheduled sometime after the coil is replaced.

2. Potentially Relevant Art

Though this invention clearly distinguishes over both prior art references, see generally Nerreter U.S. Pat. No. 8,373,417 and JP2003079596.

BRIEF SUMMARY OF THE INVENTION

This invention will utilize the Internet of Things (IoT), or more specifically a dashboard kept on the web, to remotely monitor the status of one or more MRI coils for an apparatus/MRI machine. The device, and related method of use, will detect if any such coils may have already failed, or may possibly malfunction in the imminent future—before the failure of one or more coils disrupts the flow of an MRI apparatus in operation.

Figure 9:
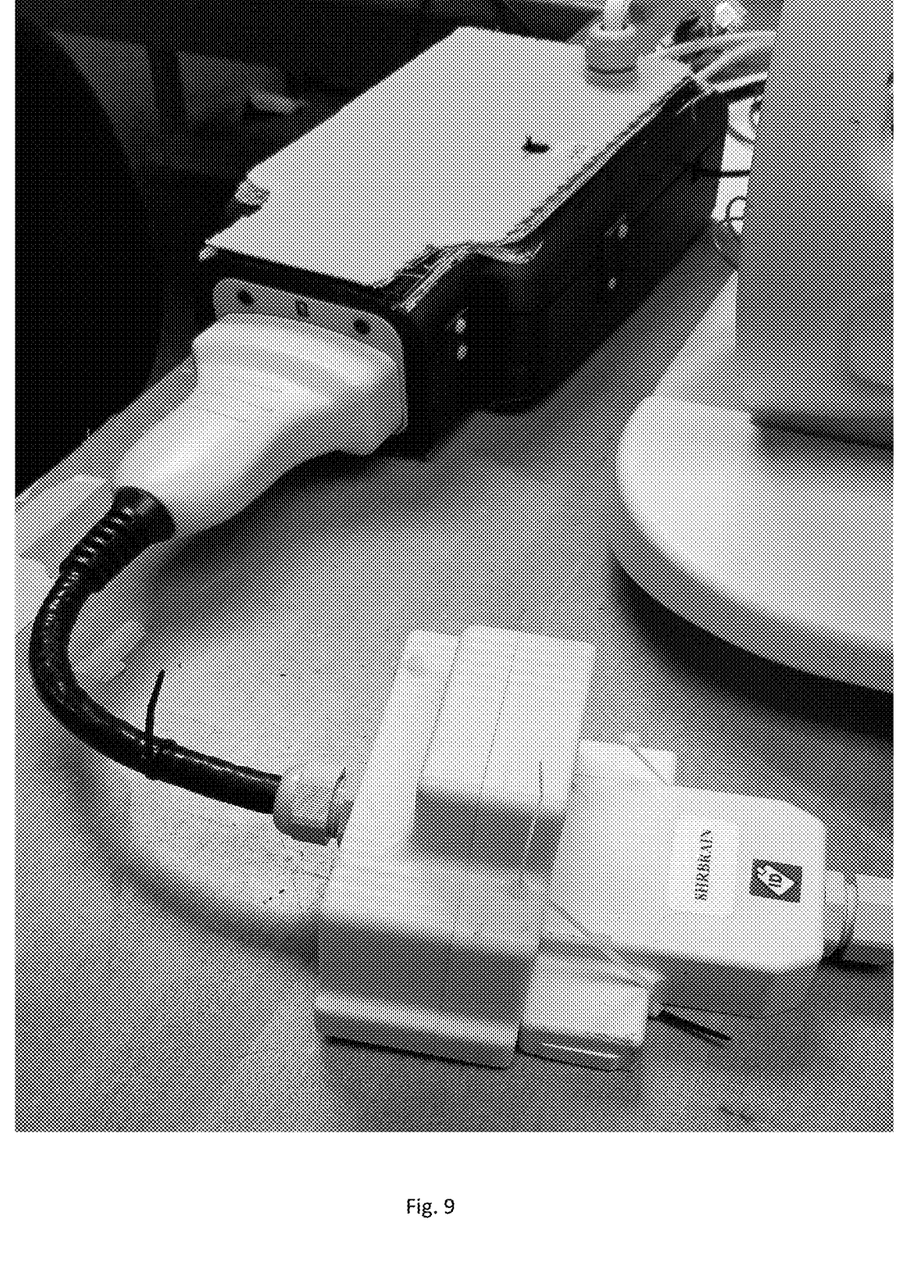
FIG. 9 is a top view photograph of one embodiment of Diagnostic Interface Device (DID) and connector cable per the present invention.

In one embodiment, the device for remotely diagnosing MRI coils comprises: (i) a Diagnostic Interface Device (or DID); and (ii) means for connecting (read: plugging) that DID to an MRI coil for testing when the MRI apparatus is not in use. The invention (both device and method) are adapted for: (a) measuring the status of certain key electrical conditions for the coil; (b) receiving a response back from the signals initially aimed at the coil in question; (c) processing those responses received; and then (d) transferring the measured electronic status (using a specific code number for the coil) to a remote storage area on the internet. Included with the foregoing DID device is a microprocessor, more specifically a microcontroller, for pushing through a transmitter one or more RF signals (or sine waves) aimed at the MRI coil to be tested. The MRI coil responds to the signal coming from the transmit antennae. Additional DID components include: a gain block (or other amplifier variety); an RF input signal mixer; a bias tee between the gain block and RF signal mixer; a signal filtration (or low-pass filter) and a DC offset. These all make up the DID hardware encapsulated in one "box" like the component pictured in accompanying FIG. 9. The system as a whole will use an analog-to-digital converter (or ADC, for short) to convert measured signal transmissions and bounce-back returns into digital data from which a center frequency will be calculated. Ideally, the device will take a plurality of readings (or data points) per coil being tested. One such variety of machine may include 20, 30, 40, 50, 60 or more points per coil (or coil sections) being tested.

The system is meant to be forgiving of accidental misreadings (or bumps). In fact, before an alarm or other warning may sound, this invention is meant to require multiple deviations (perhaps two, preferably three or more) from the return signal range observed before that MRI coil is flagged for being broken, or on the verge of a failure.

A method for predicting MRI coil failures comprises the steps of: (a) providing a Diagnostic Interface Device DID (such as is described above); (b) connecting that DID to an MRI coil to be tested/monitored; (c) sending electronic signals into the MRI coil to be tested; (d) receiving signals back from the MRI test coil; (e) controlling traffic/data control flow of PLD responses received from the MRI test coil with a DSB inside the microprocessor; (f) digitizing those flow of responses; (g) performing signal processing on these digitized MRI coil responses; and then (h) transferring the signal processed responses to a remote storage area, such as the internet, where the responses can be periodically reviewed and compared against an established norm for the coil in question so as to evaluate/diagnose said coil and/or predict if it hasn't already failed, when a soft or hard coil failure may be imminent.

BRIEF DESCRIPTION OF THE DRAWING(S) AND PHOTOGRAPH(S)

In the accompanying drawings and photographs, some numerical quantities are provided. They are suggestive or representative, however, for one sample version/variation/embodiment of this invention. Further features, objectives and advantages will become clearer when reviewing the following description of preferred embodiments made with reference to the accompanying drawings and photographs in which.

DETAILED DESCRIPTION OF THE INVENTION

The following detailed description of implementation consistent with the present invention refers to the accompanying photographs and drawings. Also, the following detailed description does not limit the invention. Instead, the scope of the invention is defined by the appended claims and equivalents.

How will it work? When the coil is not in use inside the MRI, the coil will be connected to a Diagnostic Interface Device (DID) that is a fundamental part of this invention. The coil will be plugged into the DID that will measure the status of certain key electrical conditions and transmit the electronic status of the coil (delineated by a specific code number) to a remote storage method via the internet. The information for each coil will be available to the interested service providers and end users who may wish to monitor the status of the MRI coils.

How the coils are tested: An IDT 8V97051 IC chip will generate a representative 63.87 MHz sine wave. The received response of the testing of the RF signal (sine wave) coming from the MRI coil unit under test will be pushed through an amplifier, then a bias tee, then to the RF input of a mixer. This signal is mixed with a 64 MHz sine wave to produce a 130 kHz and 127.87 MHz signal. The signal is then passed through a low-pass filter to eliminate the 127.87 MHz component. Finally, the signal goes to the ADC in the microcontroller to convert the signal into digital data. The center frequency of this signal is calculated within the microcontroller.

This remote diagnostic device, utilizing the Internet of Things (IoT) will remotely monitor MRI coils to detect when a coil is not in an operational state. It will be able to detect soft and hard failures before the coil is needed in the performance of an MRI.

This invention will have an integrated Diagnostic Interface Device (DID) that the MRI coils will plug into when they are not in use inside the MRI. The status of the coils will be transferred from the DID to the service providers and interested end users. The invention should be able to transfer data regarding the status of MRI coils via Wi-Fi module, an SD card or any other memory card.

This invention will detect: MRI coil decoupling failures; mistuned MRI coils due to mechanical failures; MRI coil preamplifier failures; intermittent MRI coil connections; and/or mistuned MRI coils due to component drift.

This invention will utilize Artificial Intelligence (AI) to track the electrical properties of coils—regardless of type or manufacturer.

EDIM—Embedded Diagnostic Interface Module

For another variation, this invention will consist of an Embedded Diagnostic Interface Module (or EDIM) built into the MRI coils of a new apparatus. By utilizing the Internet of Things (IoT) to remotely monitor the status of MRI coils, it will be possible to detect if the coil will malfunction before the coil is used in an MRI procedure.

How will the EDIM work? The MRI coil, itself, will have an embedded sensing device built in—a fundamental part of that invention. Said sensing device will measure the status of certain key electrical conditions and transmit the electronic status of the coil (delineated by a specific code number) to a remote storage area on the internet. The information for each coil will be available to the interested service providers and end users who may wish to monitor the status of the MRI coils.

Figure 1:
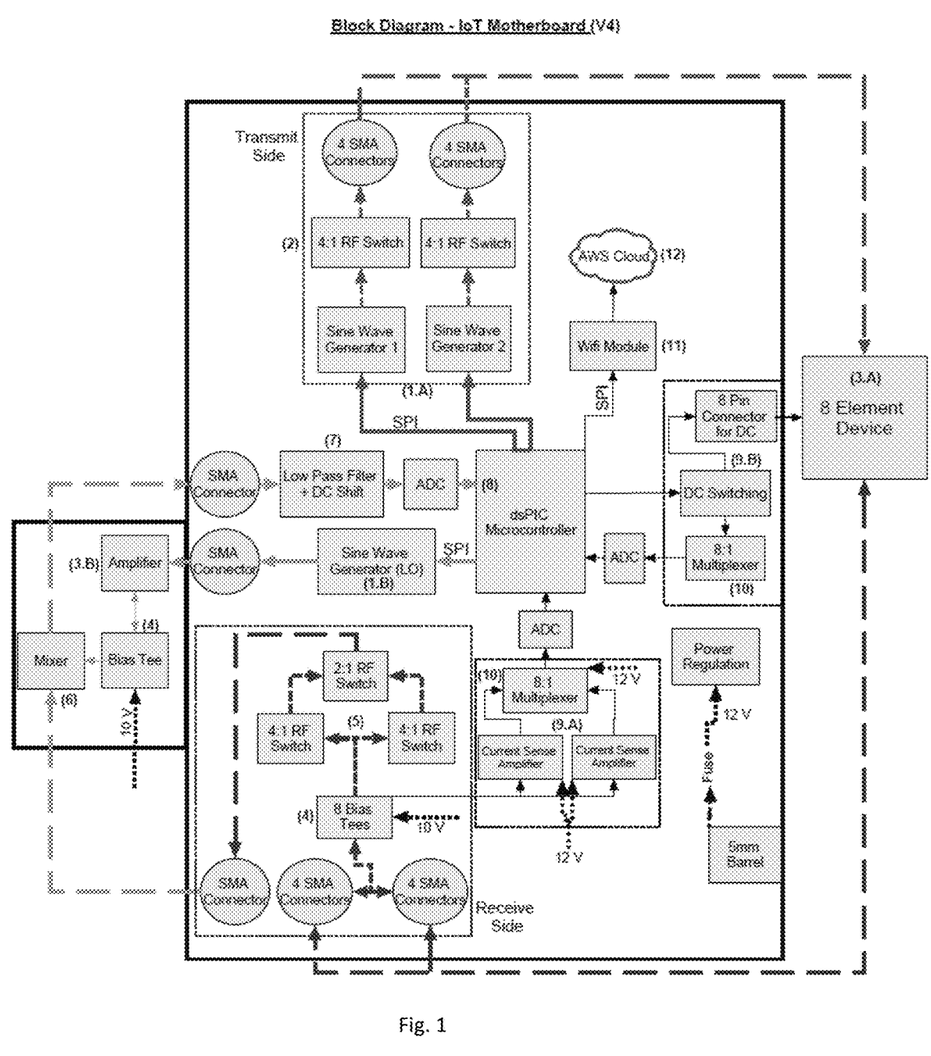
FIG. 1 illustrates a block diagram showing one preferred version of this invention. In this block diagram, it should be noted that the red arrow loop represents the section of the DID responsible for transmitting an RF signal that the test MRI coil will pick up; the blue arrow loop represents the section of the DID responsible for receiving that RF signal returned from the test MRI coil; and the green arrow loop represents the section of the DID responsible for manipulating the received RF signal for the ADC and microcontroller. Here, the received signal from the MRI coil and a local oscillator (LO) signal are mixed, filtered, then shifted so that the ADC can properly digitize said signal for the microcontroller.
Figure 2:
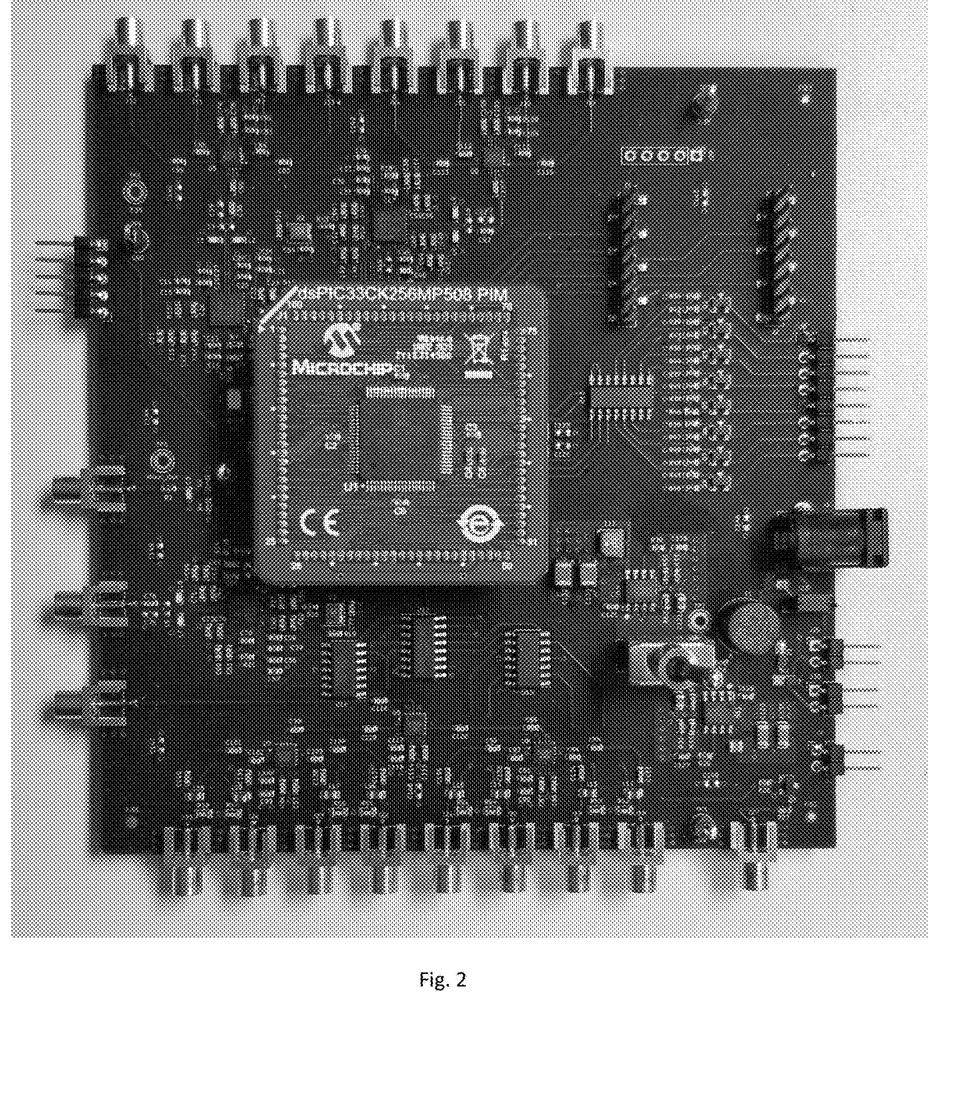
FIG. 2 illustrates a microcontroller that will be used to program the IDT chip and route the receiving signal to be digitized to the ADC. A dsPIC microcontroller will be used since it contains a 3.5 Msps Analog-to-Digital Converter (or ADC) that is sufficiently fast to digitize the returned/received signal. Note that the motherboard of this microcontroller has integrated in a sine wave generator board whose purpose is to transmit a desired RF signal to the coil element under test for exciting that element and testing its functionality. In one embodiment, the microcontroller pushes a 63.87 MHz sine wave using an IDT 8V97051 chip programmed using an SPI interface.
Figure 3:
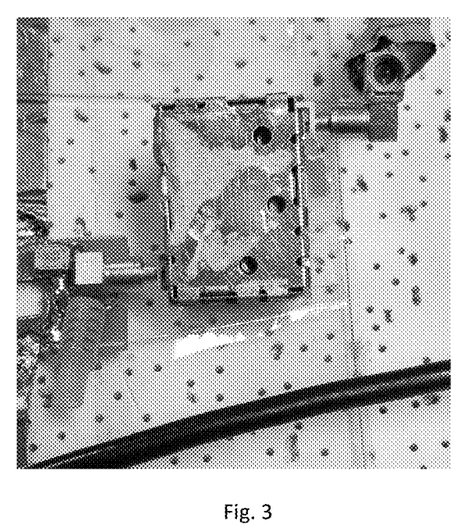
FIG. 3 is a small signal, operational RF amplifier that will be used to amplify the signal coming from a receiving antenna. Said amplifier has a narrow band gain of about 25 dB, a noise figure of less than 0.5 dB, and a small input impedance of less than 2 Ohms, all conditionally stable.
Figure 4:
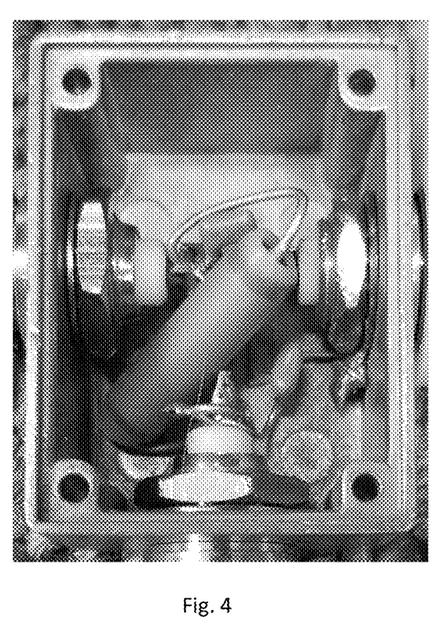
FIG. 4 is a photograph of a representative bias tee for use with one embodiment of this invention. For that tee, a 10V power supply will be connected to the DC port; the RF port will be connected to our mixer; and the RF+DC port will be connected to the op-amp. This will allow the RF signal from the antenna to pass through as well as the 10V DC signal to power the op-amp.
Figure 5:
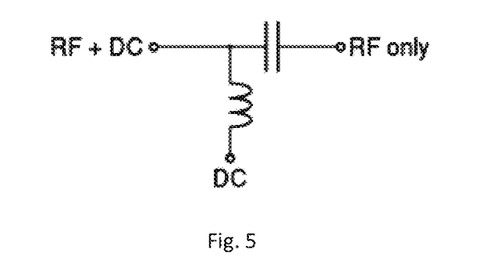
FIG. 5 is a diagrammatic representation of the circuit for the bias tee of FIG. 4.
Figure 6:
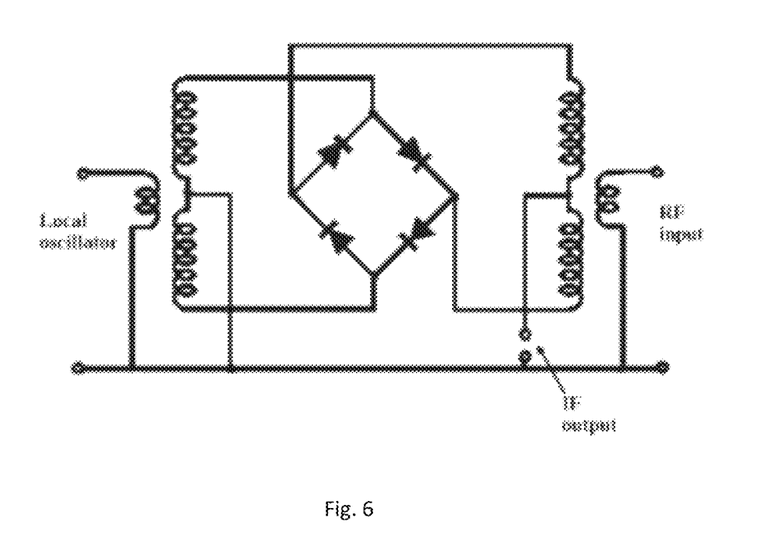
FIG. 6 illustrates one embodiment of mixer that this invention will use to down convert the signal for the present invention. In that representative embodiment, the RF signal coming in will be a 63.87 MHz signal and the local oscillator will be providing a 64 MHz signal. The two IF signals coming out will be around 130 kHz and 127.87 MHz. It should be noted, however, that these values are for one representative example of DID device and the scope of this invention should not be limited to same.
Figure 7:
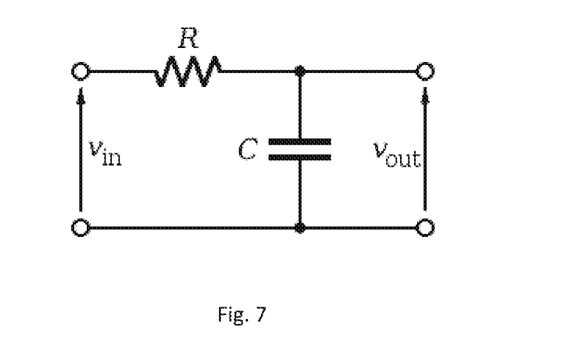
FIG. 7 illustrates a representative signal filtration (i.e., low pass filter) that will be used to eliminate the 127.87 MHz signal as current versions of this invention are unable to do anything meaningful with that signal since it is too fast for the aforementioned ADC. Such a filter will fully eliminate this component.
Figure 8:
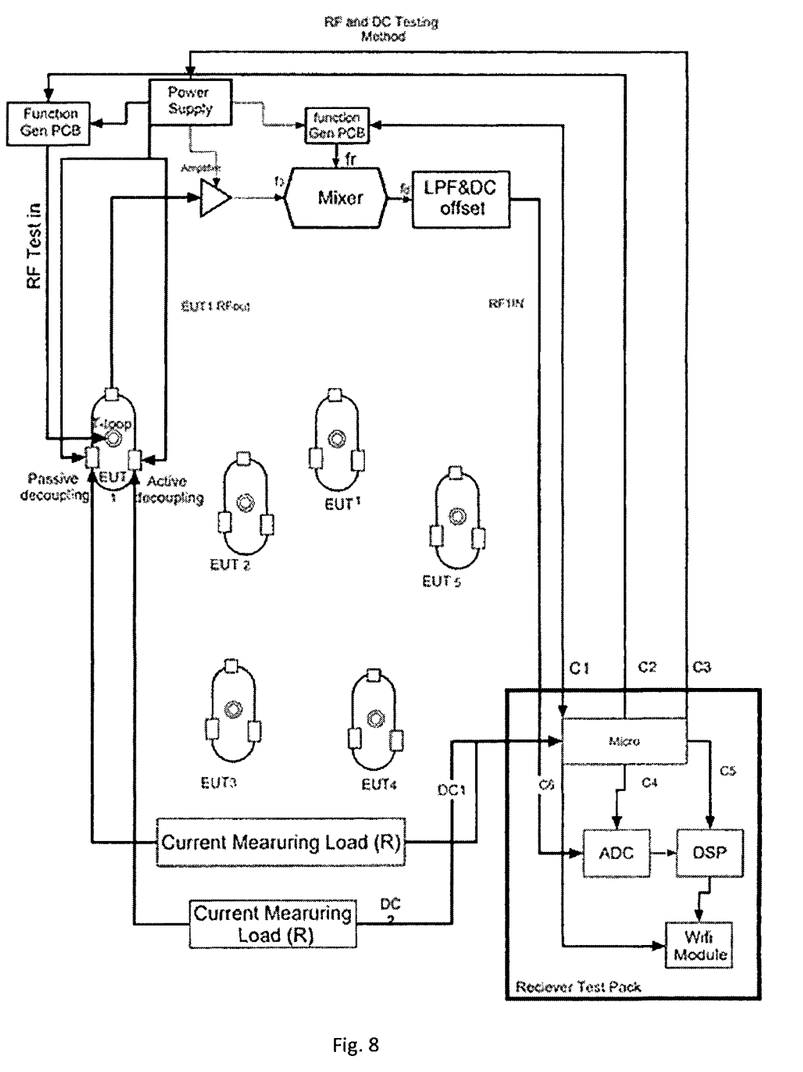
FIG. 8 is a high-level flowchart representing one preferred method of RF/DC coil testing per the present invention.

This new embedded device will examine both sides of the coil parameters (both RF and DC) where the following high-level steps of test events will be performed (Preferably, all activities in this device will be controlled by a central control unit such as a microcontroller for controlling signal activation and traffic allowance per FIG. 8):

For RF:

Each Element Under Test (EUT) in the coil will have an assigned small signal Amplifier and a drive point. An RF signal will be transmitted at a desired frequency into the EUT. The element(s) of the MRI coil under test will produce a response to the transmitted RF signal and push that response into the EDIM.

the received signal will then go through a mixer with an LO of desired frequency generated by this RF signal.

the output of the mixer (IF) will be+/−mixed signal in and will go through an LPF where signal is DC offset to go to an ADC digital signals will then be analyzed via a DSP module data will then get packaged and sent to a WIFI module where that data will be pushed to the cloud. In the internet cloud, this system will have on a dashboard, an algorithm for analyzing these data points to determine the present condition of a coil element under test.

For DC:

after finishing the RF test, a voltage will be sent each decoupling block in EUT to determine part integrity and functionality.

a DC Signal received for each decoupling block will be pushed to a controlling unit (microcontroller) for packaging this data with the RF data before sending to the cloud. This data will be decoded at cloud level and analyzed to determine DC functionality of each decoupling block.

Per the accompanying Figs., this is one example (part selection) of implementing an EDIM IoT Device:

EDIM Example

RF Testing
1. The dsPIC33CK256MP508 microcontroller is used to control three 8V97051 Sine Wave Generator chips via 2 Serial Peripheral Interface (SPI) ports.
   A. One SPI port is used to control either Sine Wave Generator 1 or 2 depending on the element we are testing. The Sine Wave Generators output frequencies ranging from 56 MHz to 76 MHz in 0.4 MHz intervals. This gives us 50 points.
   B. This $3^{rd}$ Sine Wave Generator serves as a Local Oscillator (LO) and outputs frequencies ranging from 55.99 MHz to 75.99 MHz in 0.4 MHz intervals. This gives us 50 points.
2. There are two HMC7992 RF Switches to determine which element in the MRI coil device to send a test signal to.
3. The corresponding element responds to said test signal.
   A. The 8-element device contains the elements under test.
   B. The LO signal goes through an amplifier similar to the one in the 8-element device in order to get both signal amplitudes to match.
4. The RF signals, the LO signal, and a 10V DC supply are connected to bias tees. This is so the individual amplifier and the amplifiers in the 8-element device are powered via a 10V supply while also amplifying the RF and LO signals.
5. There are additional HMC7992 RF switches used to determine which element we are testing.
6. The ZFM-150+ mixer outputs a modulated signal, a high and low frequency signal. The low frequency signal should always be around 10 kHz. The high frequency signal will always be filtered out since we cannot analyze this signal.
7. A first order low pass filter is used to eliminate the high frequency signal. Then the low frequency signal gets shifted up via a resistor ladder. This is needed since the ADC on the dsPIC33CK256MP508 cannot see negative voltages.
8. Once the data is digitized, FFT analysis is done to determine the strength of the 10 kHz signals for each of the 50 points.

Preamplifier and De-Coupling
9. The preamplifier and de-coupling currents are also measured:
   A. The preamplifier currents are measured using two MAX4378HASD+T current sense amplifiers.
   B. The DC switching is used to control which de-coupling current to test.
10. Two HCF4051YM013TR 8:1 multiplexers are used to decide which element's preamplifier/de-coupling current to test.
11. The $3^{rd}$ SPI port is used to send the power and frequency data to Wi-Fi module AC164164. The Wi-Fi module pushes that data into the Amazon Web Services (AWS) Cloud.
12. The backend infrastructure is built from AWS cloud services. A data processing engine is built with the help of AWS IoT core and Lambda. AWS is also used to store data and deploy the dashboard application. In the cloud, we analyze data (RF&DC) coming real time from CUT (coil under test) and determine status of all functional parameter of the coil.

The foregoing employs the following, representative Power Management

| dsPIC33CK256MP508 Microcontroller | 10 V | 100 mA |
|---|---|---|
| 8V97051 Sine wave generators | 3.3 V | 390 mA |
| Op-Amps | 10 V | 70 mA |
| AC164164 Wi-Fi module | 3.3 V | 20 mA |
| DC Shifting Circuit | 3.3 V | 50 mA |
| Active Decoupling | 10 V | 40 mA |

With the preceding Embedded Diagnostic Interface Module (EDIM), it will remotely monitor MRI coils and detect when a coil is not in an operational state utilizing the Internet of Things (IoT). It will be able to detect both soft and hard failures before the coil is needed in the performance of an MRI.

This alternate embodiment of the present invention will have an integrated Diagnostic Interface Module (DIM) thus giving it an ability to perform as a self-testing device. The status of the coil will be transmitted to a cloud services app for Applicants' analytics modules to derive conclusions and recommendations from the DIM to MRI service providers and other interested end users.

This version will be able to transmit data regarding the status of the subject MRI coil via a Wi-Fi module (internal or external), an SD card or other memory card.

This invention will detect both soft and hard failures. Examples of soft failures include: poor image quality due to Signal-to-Noise ratios below specification or various image artifacts while examples of a hard failure include a complete lack of an image.

The Embedded Diagnostic Interface Module, or EDIM, will detect: MRI coil decoupling failures, mistuned MRI coils due to mechanical failures, MRI coil preamplifier failures, intermittent connection detections of MRI coils, and mistuned MRI coils due to component drift. It will utilize Artificial Intelligence (AI) to track the electrical properties of coils and learn to predict when a coil will fail before the failure occurs.

HDIM—Handheld Digital Interface Module

For a handheld version, also known as a Handheld Diagnostic Interface Module (HDIM), it will utilize the Internet of Things (IoT) to allow field service personnel to monitor MRI coils on site. Such personnel can simply plug into any given MRI coil for detecting when that coil is not fully operational. The HDIM will be able to detect both soft and hard failures before the coil is needed in the performance of an MRI. This design will allow field service engineers to troubleshoot more quickly. It will also give such engineers the capability of repairing or replacing an MRI coil before it fails.

The device will examine both sides of the coil parameters (both RF & DC) where the following high-level description of test event steps may take place (Keep in mind all activities with this device may be controlled by a central control unit such as a microcontroller for controlling signal activation and traffic allowance. See, FIG. 8):

For RF:
Each Element Under Test (EUT) in the coil will have an assigned small signal amplifier and a drive point. An RF signal will be transmitted at a desired frequency into the EUT. The MRI coil will produce a response to the transmitted RF signal and push that response into the HDIM.

the received signal then will go through a mixer with an LO of desired frequency generated by our RF signal.

the output of the mixer (IF) will be +− of mixed signal in and will go through a LPF where signal is then DC offset to go to an ADC digital signals are then analyzed via a DSP module data then gets packaged and sent to WIFI module where it will be pushed to the cloud in the cloud, we will have an algorithm that will review data points for determining the condition of an MRI coil element under test.

For DC:
after finishing the RF test, this version of the system will send a voltage to each decoupling block in EUT to determine part integrity and functionality.

the DC Signal received for each decoupling block will be pushed to a controlling unit (or microcontroller) to package this data with the RF data before sending to the cloud. That data will be decoded at cloud level and analyzed to determine DC functionality of each decoupling block.

Per the accompanying Figs., this is one example (part selection) of implementing an HDIM IoT Device:

HDIM Example

RF Testing
1. The dsPIC33CK256MP508 microcontroller is used to control three 8V97051 Sine Wave Generator chips via 2 Serial Peripheral Interface (SPI) ports.
   A. One SPI port is used to control either Sine Wave Generator 1 or 2 depending on the element we are testing. The Sine Wave Generators output frequencies ranging from 56 MHz to 76 MHz in 0.4 MHz intervals. This gives us 50 points.
   B. This $3^{rd}$ Sine Wave Generator serves as a Local Oscillator (LO) and outputs frequencies ranging from 55.99 MHz to 75.99 MHz in 0.4 MHz intervals. This gives us 50 points.
2. There are two HMC7992 RF Switches to determine which element in the MRI coil device to send a test signal to.
3. The corresponding element responds to said test signal.
   A. The 8-element device contains the elements under test.
   B. The LO signal goes through an amplifier similar to the one in the 8-element device in order to get both signal amplitudes to match.
4. The RF signals, the LO signal, and a 10V DC supply are connected to bias tees. This is so the individual amplifier and the amplifiers in the 8-element device are powered via a 10V supply while also amplifying the RF and LO signals.
5. There are additional HMC7992 RF switches used to determine which element we are testing.
6. The ZFM-150+ mixer outputs a modulated signal, a high and low frequency signal. The low frequency signal should always be around 10 kHz. The high frequency signal will always be filtered out since we cannot analyze this signal.
7. A first order low pass filter is used to eliminate the high frequency signal. Then the low frequency signal gets shifted up via a resistor ladder. This is needed since the ADC on the dsPIC33CK256MP508 cannot see negative voltages.
8. Once the data is digitized, FFT analysis is done to determine the strength of the 10 kHz signals for each of the 50 points.

Preamplifier and De-Coupling
9. The preamplifier and de-coupling currents are also measured:
    A. The preamplifier currents are measured using two MAX4378HASD+T current sense amplifiers.
    B. The DC switching is used to control which de-coupling current to test.
10. Two HCF4051YM013TR 8:1 multiplexers are used to decide which element's preamplifier/de-coupling current to test.
11. The 3$^{rd}$ SPI port is used to send the power and frequency data to Wi-Fi module AC164164. The Wi-Fi module pushes that data into the Amazon Web Services (AWS) Cloud.
12. The backend infrastructure is built from AWS cloud services. A data processing engine is built with the help of AWS IoT core and Lambda. AWS is also used to store data and deploy the dashboard application. In the cloud, we analyze data (RF&DC) coming real time from CUT (coil under test) and determine status of all functional parameter of the coil.

Similar to the EDIMI system above, this HDIM employs the following representative Power Management:

| | | |
|---|---|---|
| dsPIC33CK256MP508 Microcontroller | 10 V | 100 mA |
| 8V97051 Sine wave generators | 3.3 V | 260 mA |
| Op-Amps | 10 V | 70 mA |
| AC164164 Wi-Fi module | 3.3 V | 20 mA |
| DC Shifting Circuit | 3.3 V | 50 mA |
| Active Decoupling | 10 V | 40 mA |

The Handheld Diagnostic Interface Module (HDIM) version of this invention will utilize the Internet of Things (IoT) to allow field service personnel to monitor MRI coils on site and detect when a coil is not fully operational. It will be able to detect both soft and hard failures before the coil is needed in the performance of an MRI.

This device (and related method of use) will allow field service engineers to troubleshoot more quickly. It will also give them the capability to repair or replace an MRI coil before it fails.

Ideally, this embodiment of the present invention will be in the form of a handheld device that will have an integrated Diagnostic Interface Module (DIM) thus giving it the ability to perform as a self-testing device. The status of any tested coil may be viewed on site and will be transmitted to a cloud services app for analytics modules to derive conclusions and recommendations from the DIM to MRI service providers and other interested end users.

This invention will transmit data regarding the status of the subject MRI coil via Wi-Fi module, an SD card or other memory card. It will detect both soft and hard failures. Examples of a soft failure including poor image quality due to Signal-to-Noise ratios below specification or various image artifacts. And examples of a hard failure including a complete lack of an image.

The Handheld Diagnostic Interface Module (HDIM) version of this invention should be able to detect: MRI coil decoupling failures, mistuned MRI coils due to mechanical failures, MRI coil preamplifier failures, intermittent connection detections of MRI coils and/or mistuned MRI coils due to component drift. The invention will utilize Artificial Intelligence (AI) to track the electrical properties of coils and learn to predict when a coil will fail before the failure occurs.

Having described the best modes currently known for practicing this device/system and method, it is to be understood that the scope of this invention may be further described by the attached claims.

SEQUENCE LISTING

Not applicable.

What is claimed is:

1. A device for remotely diagnosing an MRI coil comprises:
    (a) a Diagnostic Interface Device (DID) that includes:
        (i) a section for transmitting one or more electrical testing signals to the MRI coil when the MRI coil is not in use;
        (ii) a section for receiving responses from the MRI coil to the electrical testing signals transmitted by the DID to the MRI coil;
        (iii) a section for manipulating the MRI responses received, said manipulating section including: a gain block, an RF signal mixer, a signal filtration and a DC offset;
        (iv) a section for digitizing the manipulated responses received from the MRI coil;
        (v) a section for performing signal processing on the digitized, MRI responses received; and
        (vi) a section for transferring signal processed responses for the MRI coil to a remote storage area and conducting periodic comparative analytics on the transferred signal processed responses; and
    (b) means for connecting the DID to the MRI coil.

2. A device for determining whether a coil of an MRI apparatus under test has failed or may soon fail, said device comprising:
    (a) a Diagnostic Interface Device (DID) that includes:
        (i) a section for transmitting to the coil under test, when the MRI apparatus is not in use, one or more electrical test signals including:
            one or more RF signals, and
            one or more signals for evaluating DC status of the coil under test;
        (ii) a section for receiving from the coil under test RF signal responses to the RF signals transmitted by the DID;
        (iii) a section for manipulating the RF signal responses received from the coil under test with at least one programmable unit/logic device selected from the group consisting of a microcontroller, a Field Programmable Gate Array (FPGA), a Programmable Logic Device (PLD) and a System on a Chip (SoC);
        (iv) a section for digitizing the manipulated RF signal responses received;
        (v) a section for performing signal processing on the digitized, manipulated RF signal responses received;
        (vi) a section for transferring signal processed responses for the coil under test to a dashboard using at least one of: a WiFi module, an SD card and a memory card, said dashboard adapted for conducting periodic comparative analytics on the transferred signal processed responses; and determining whether the coil under test has failed or may soon fail; and
    (b) means for connecting the DID to the coil under test.

3. A method for predicting failure of an MRI coil, said method comprising the steps of:
(a) providing a Diagnostic Interface Device (DID) that includes:
  (i) a section for transmitting to the MRI coil when not in service a plurality of electronic signals including: test RF signals, and
   one or more signals for evaluating DC status of the MRI coil;
  (ii) a section for receiving responses of the MRI coil to the plurality of electronic signals transmitted by the DID;
  (iii) a section for manipulating the MRI coil responses received with at least one programmable unit/logic device selected from the group consisting of a microcontroller, a Field Programmable Gate Array (FPGA), a Programmable Logic Device (PLD) and a System on a Chip (SoC);
  (iv) a section for digitizing the MRI coil responses manipulated so that the programmable unit/logic device may perform signal processing thereon; and
  (v) a section for transferring the digitized, signal processed responses for the MRI coil to a remote storage area so that periodic comparative analytics may be conducted thereon, said transmitting section including at least one of: a WiFi module, an SD card and a memory card;
(b) connecting the DID to the MRI coil;
(c) sending the plurality of electronic signals to the MRI coil;
(d) receiving the responses received by the DID from the plurality of electronic signals transmitted to the MRI coil;
(e) manipulating the responses received with the programmable unit/logic device;
(f) digitizing the manipulated responses received;
(g) performing signal processing on the digitized, manipulated responses;
(h) transferring the signal processed responses to a remote storage area on the internet; and
(i) conducting periodic comparative analytics on the transferred signal processed responses to remotely determine whether the MRI coil is functioning satisfactory, has already failed or is susceptible to imminent failure.

4. The device of claim 1 wherein transmitting section (i) includes means for aiming at least one RF signal toward the MRI coil being diagnosed.

5. The device of claim 1 wherein transmitting section (i) further includes means for transmitting one or more signals to evaluate DC status of the MRI coil.

6. The device of claim 1 wherein receiving section (ii) includes means for capturing a waveform frequency response from the MRI coil.

7. The device of claim 1 wherein manipulating section (iii) includes at least one programmable unit/logic device selected from the group consisting of a microcontroller, a Field Programmable Gate Array (FPGA), a Programmable Logic Device (PLD) and a System on a Chip (SoC).

8. The device of claim 1 wherein the gain block for manipulating section (iii) includes an amplifier.

9. The device of claim 1 wherein manipulating section (iii) further includes means for adding a local oscillator (LO) signal to the MRI coil response received by the DID.

10. The device of claim 1 wherein signal processed response transferring section (vi) includes an internal or external WiFi module.

11. The device of claim 1 wherein signal processed response transferring section (vi) includes an SD card or memory card.

12. The device of claim 1, which can be used to detect soft or hard failures in the MRI coil.

13. The device of claim 2 wherein manipulating section (iii) includes one or more of: a gain block, an RF signal mixer, a signal filtration and a DC offset.

14. The device of claim 2, which can be used to predict soft or hard failures in the MRI coil.

15. The method of claim 3 wherein step (e) includes the sub-step of adding a local oscillator (LO) signal to the responses received.

16. The method of claim 3 wherein manipulating section (iii) of the DID further includes one or more of: a gain block, an RF signal mixer, a signal filtration and a DC offset.

17. The method of claim 3 wherein the WIFI module is internal to the DID.

18. The method of claim 3 wherein the wherein the MRI coil may have experienced or may be susceptible to a soft or hard failure.

19. The device of claim 4 wherein transmitting section (i) further includes a sine wave generator.

20. The device of claim 13, wherein manipulating section (iii) further includes means for adding a local oscillator (LO) signal to the RF signal responses received from the coil under test.

* * * * *